US006221375B1

(12) United States Patent
Howse

(10) Patent No.: US 6,221,375 B1
(45) Date of Patent: *Apr. 24, 2001

(54) PESTICIDAL OR HERBICIDAL COMPOSITIONS

(75) Inventor: Philip Edwin Howse, Gosport (GB)

(73) Assignee: University of Southampton, Southampton (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,865

(22) PCT Filed: Mar. 12, 1997

(86) PCT No.: PCT/GB97/00683

§ 371 Date: Jul. 21, 1998

§ 102(e) Date: Jul. 21, 1998

(87) PCT Pub. No.: WO97/33472

PCT Pub. Date: Sep. 18, 1997

(30) Foreign Application Priority Data

Mar. 12, 1996 (GB) .................................................. 9605203

(51) Int. Cl.[7] .......................... A01N 25/26; A01N 25/00; A01N 25/08; A61K 9/50

(52) U.S. Cl. .......................... 424/417; 424/405; 424/409; 424/418; 424/419; 424/420; 424/421; 424/490; 424/498

(58) Field of Search .................................... 424/405, 409, 424/489–502, 417–421

(56) References Cited

U.S. PATENT DOCUMENTS

| | | | | |
|---|---|---|---|---|
| 4,685,620 | * | 8/1987 | Law et al. | 239/3 |
| 4,971,796 | * | 11/1990 | Sjogren | 424/408 |
| 5,283,060 | | 2/1994 | Shieh | 424/93 L |
| 5,346,704 | * | 9/1994 | Lajoie | 424/717 |
| 5,358,863 | | 10/1994 | Quimby, Jr. et al. | 435/178 |
| 5,807,566 | * | 9/1998 | De Vlieger et al. | 424/409 |

FOREIGN PATENT DOCUMENTS

| | | | |
|---|---|---|---|
| 0018119 A1 | 10/1980 | (EP) | A01N/25/26 |
| 0529975 A1 | 3/1993 | (EP) | A01N/47/36 |
| WO83/00799 A1 | 3/1983 | (WO) | A01N/25/26 |
| WO94/00980 A1 | 1/1994 | (WO) | A01M/1/20 |
| WO97/07676 A1 | 3/1997 | (WO) | A01N/25/26 |

OTHER PUBLICATIONS

Patent Abstracts of Japan, vol. 15, No. 60, C–805, abstract of JP,A,2–288803, (Nov. 28, 1990).

* cited by examiner

*Primary Examiner*—Russell Travers
*Assistant Examiner*—Shengjun Wang
(74) *Attorney, Agent, or Firm*—Fish & Richardson P.C.

(57) ABSTRACT

A pesticidal or herbicidal composition in particulate form which comprises composite particles. Each of said particles contains a core of an inert substance having a pesticidal herbicide associated therewith and a coating of an electrically resistive material around the core. The particles may also include a second pesticidal material adhering to the electrically resistive coating. The particles carry an electrostatic charge.

10 Claims, 3 Drawing Sheets

FIG. 2 The Effect of Electrostatic Powder on $SiO_2$ and Sulfluramid Admixtures
a. 90% Silicon Dioxide, 10% Sulfluramid (Control)
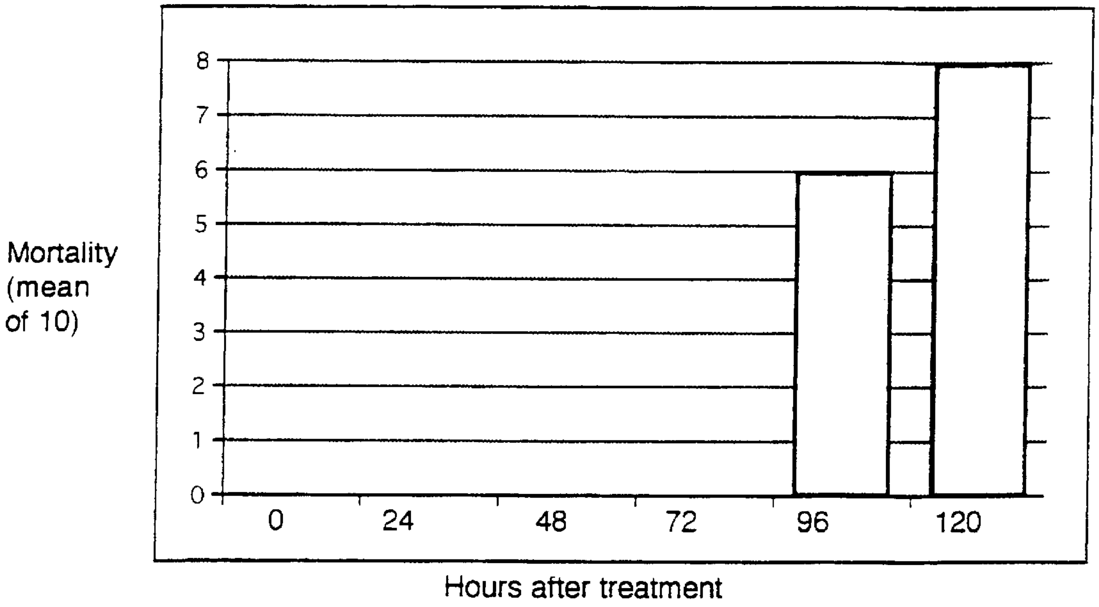
b. 80% Carnauba Wax, 10% Silicon dioxide, 10% Sulfluramid
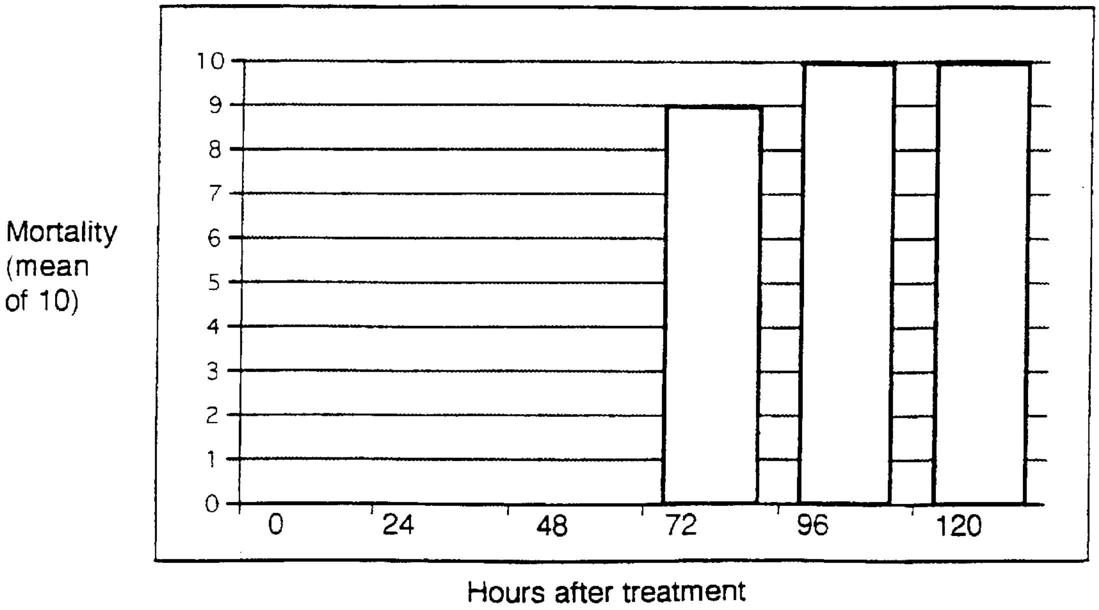

FIG. 3 The Effect of Electrostatic Powder on Chitosan and Sulfluramid Admixtures
a. 90% Chitosan, 10% Sulfluramid (Control)
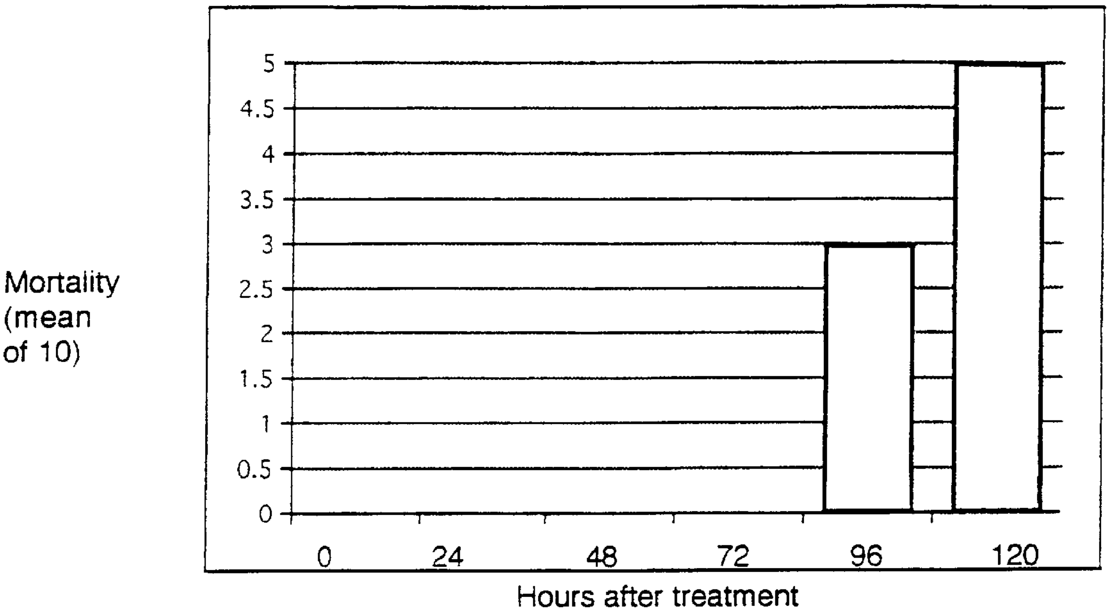
b. 80% Carnauba Wax, 10% Chitosan, 10% Sulfluramid
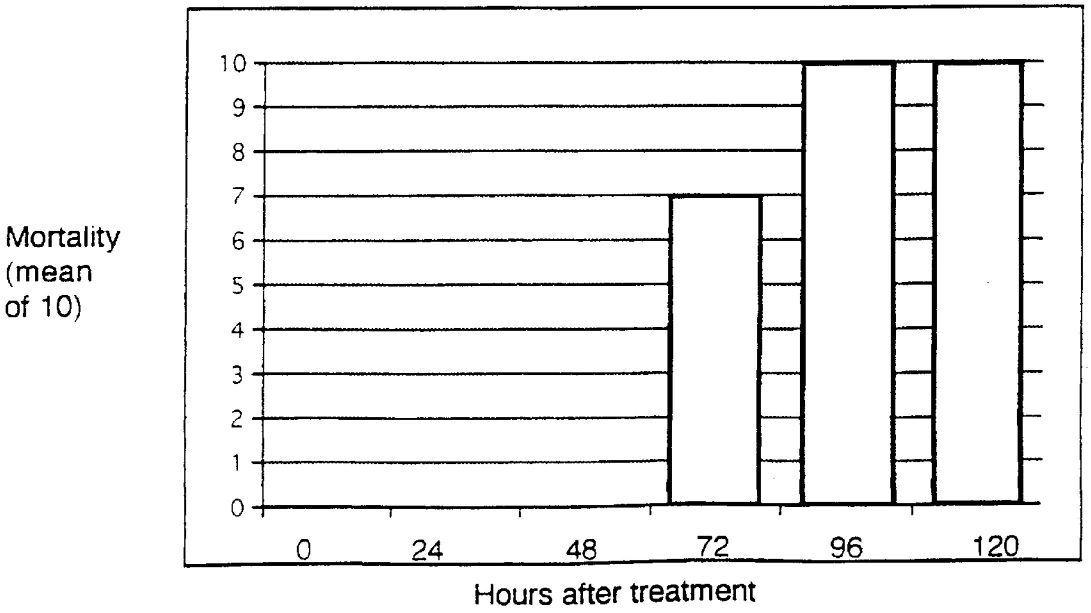

PESTICIDAL OR HERBICIDAL COMPOSITIONS

This application is a 371 of PCT/GB97/00683, filed Mar. 12, 1997, which claims priority of GB9605203.0, filed Mar. 12, 1996.

BACKGROUND OF THE INVENTION

The present invention relates to pesticidal or herbicidal compositions.

The most common domestic insect pests are houseflies, mosquitoes and cockroaches.

The common housefly, *Musca domestica*, occurs throughout the world in domestic situations. Along with similar species, such as, the lesser housefly, blowflies and flesh flies, it contaminates food and spreads diseases, such as, typhoid and cholera, and also carries the eggs of parasitic worms.

The housefly is also a problem on refuse tips and is becoming a progressively greater nuisance in agriculture, where it breeds in deep litter breeding units for poultry and other animals.

The cockroach is ubiquitous in urban situations in the tropics and sub-tropics and is common in heated buildings in Britain, the rest of Europe and North America where food is prepared. Large cockroach populations are found in sewers and drains and many disease organisms have been isolated from them.

The mosquito is both a severe nuisance pest and vastly important as a vector for blood-borne diseases, such as, malaria, yellow fever, dengue and the like.

Control of those insect pests is becoming more urgent as human populations increase and provide more resources for them to breed.

International Patent Application No. WO94/00980 described the ability of electrostatically charged powders to adhere to an insect cuticle, to a surface of a plant or to a surface of an insect trap. However, insecticidal powders, for example magnesium silicate or silica particles impregnated with an insecticide, do not have the necessary characteristics either to be electrostatically charged or to retain such an electrostatic charge and therefore the particles do not become attached firmly to an insect cuticle, to the surface of a plant, or to a surface of an insect trap.

Herbicidal compositions which are in a particulate form also suffer the disadvantage that the herbicidal particles do not adhere firmly to the plants onto which they are sprayed or dusted.

We have now developed pesticidal or herbicidal compositions which are in particulate form and which have improved adherent properties so that they adhere more firmly to the insect, plant or surface onto which they are sprayed or dusted.

SUMMARY OF THE INVENTION

Accordingly, the present invention provides a pesticidal or herbicidal composition in particulate form which comprises composite particles each comprising a core of an inert substrate having a pesticide or herbicide associated therewith, and a coating of an electrically resistive material around the said core, the particles carrying an electrostatic charge.

BRIEF DESCRIPTION OF THE DRAWINGS

FIG. 2 is a graph showing the mean mortality of cockroaches resulting from the tests of Example 1.

FIG. 3 is a graph showing the mean mortality of cockroaches resulting from the tests of Example 2.

DETAILED DISCLOSURE

Figure 1:
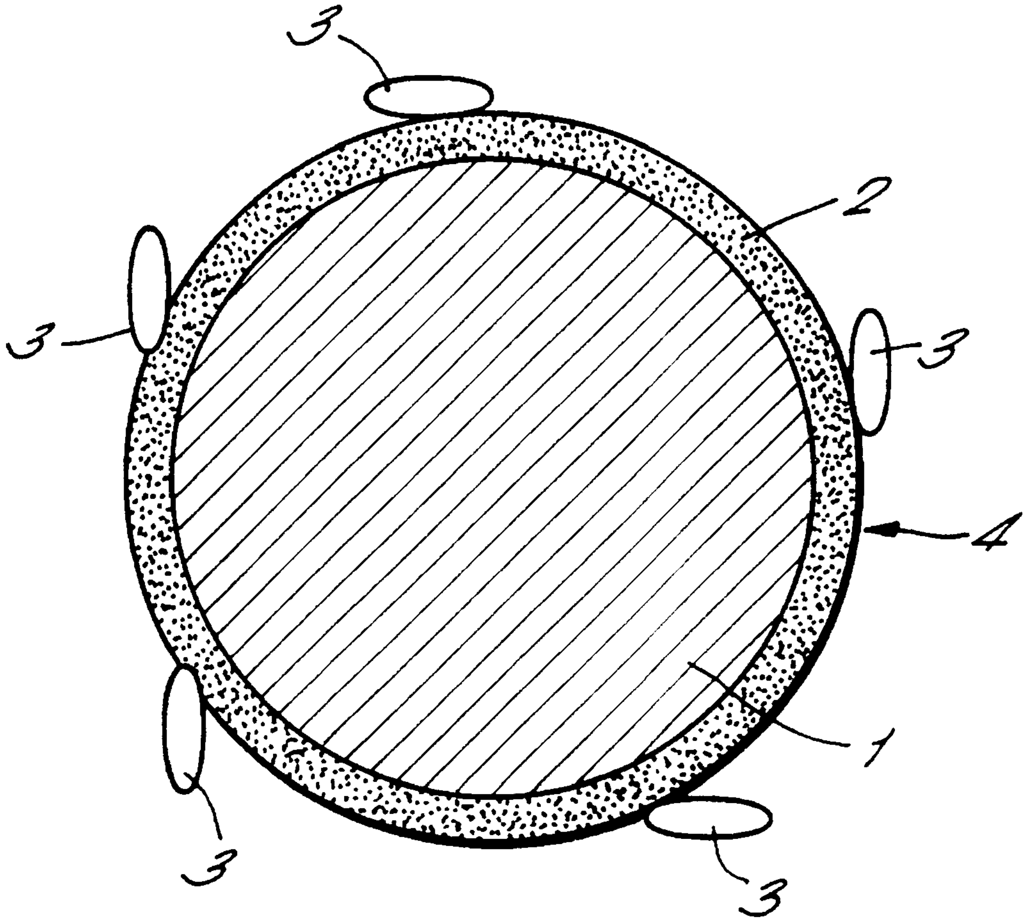
FIG. 1 illustrates a composite particle according to this invention.

By the term "pesticide" as used herein is meant any substance which can be used in the control of agricultural, natural environmental and domestic pests, such as insects. Included within this term, therefore, are naturally occurring or synthetic chemical insecticides, fungicides, acaricides, insect growth regulators and chemosterilants; entomopathogens such as bacteria, viruses and fungi; parasites; and behaviour modifying chemicals such as pheromones, allomones and kairmones. By the term "herbicide" as used herein is meant any substance which can be used in agriculture to control or modify plant growth.

The compositions of the present invention comprise a core of an inert substrate, i.e. a material which acts merely as a carrier for the pesticide or herbicide and which is chemically and biologically inert. The inert substrate is preferably porous and highly absorbent. Suitable examples of such materials are silicon dioxide, magnesium silicate (talc), diatomaceous earth, cellulose or natural or synthetic polymers such as chitin, chitosan or rubber. The inert substrate may have the pesticide or herbicide associated with it by impregnation into it, or may have the pesticide or herbicide associated with it in some other way for example by adsorption or absorption thereon.

The cores of the composite particles are coated with a coating of an electrically resistive material, i.e. a material which readily accepts an electrical charge, such as a wax, a lipid, a natural or synthetic resin or a natural or synthetic polymeric material. Examples of waxes which may be used are Carnauba Wax, paraffin waxes, candelilla wax and bees' wax. Examples of polymeric coating materials are polytetrafluoroethylene, or ethylenic polymers. Examples of resins are shellac and synthetic acrylic resins. An example of a lipid which may be used is lecithin.

The composite particles of the present invention will generally have a particle size in the range of form 1 to 100 $\mu$m, preferably 20 to 60 $\mu$m. If the particles are too small then they become hazardous to human health, whilst if they are too large they will then tend to fall off the insect, plant or other surface to which they are applied either because of gravitional forces and/or because there will be insufficient electrostatic attraction. The thickness of the coating of the electrically resistive material is not critical, provided that it surrounds the core of the particles and can readily accept an electric charge. Generally, the coating material will comprise at least 0.1% by volume, preferably 5 to 25% by volume of the particles and the core will comprise up to 99.9% by volume, preferably 75 to 95% by volume of the particles.

The coating of electrically resistive material may be applied to the cores of the particles by any suitable coating technique such as by fluidised bed coating, spraying or mixing.

The amount of pesticide or herbicide which is impregnated into or associated with the inert substrate will generally comprise at least 0.1% by weight of the inert substrate. The amount of the pesticide or herbicide will depend upon the intended release rate from the composition and the length of intended duration of release. It will also depend upon the nature of the electrically resistive coating and other factors.

It is known that insects carry an electrostatic charge. In the case of the cockroach, the outside of its cuticle is positively charged, with an electrostatic gradient across the cuticle (Beament, J. W. L. in *Nature Lond.* Vol. 191, 1961, pp 217–221).

Accordingly, it is preferred if the particles of the compositions of the invention are electrostatically charged to have an opposite polarity to that of the pest against which they are targeted. In this manner, the adhesion of the charged particles to the pest is improved.

The pesticide which is used in the present invention may be specifically targeted to the control of particular pests. For example, an insecticide may be applied to sexually mature male insects so that it spreads among the rest of the population during mating or by contact during swarming. The insecticide is unlikely to spread to other species of insect when transmitted in this way.

Each pesticide may be chosen to have a narrow spectrum of action. Entomopathogens are particularly well suited to this. A further embodiment is to use as the pesticide a specific attractant to attract insects to the composition. For example, the attractant may be a sexual pheromone. Furthermore, a sexual attractant pheromone may be used to produce male confusion. This technique depends on the very high sensitivity of male insects to volatile sex attractants produced by females of the same species. (In a few cases the male produces the attractant). The female pheromone affects the male guidance system which depends on flying upwind in an odour laden air current, thereby disrupting mating by preventing the males from locating the females.

Alternatively, a surface on which the insects may land is coated with electrostatically charged particles containing a volatile pheromone. The particles are then picked up by the insect from the surface. The particles picked up in this way are then transferred to the antennae or other parts of the insect bodies either by exploratory movement or during cleaning. The particles remain in place and continue to release pheromone, the coating on the particle ensuring good attachment and controlling the release rate. Due to habituation or saturation of the antenna receptors by the pheromone emission, the insects are unable to orientate with respect to trace emissions of pheromone from female insects in the air. Mating fails to occur and eggs laid by the females are infertile. Furthermore, the males themselves act as female mimics, diverting uncontaminated males away from calling females.

In a particular embodiment of the invention the electrically resistive coating is smooth. The smoothness of the coating will depend upon the nature of the coating material and the coating technique used. Accordingly, insects or mites which contact the smooth coating on charged particles get the particles onto their feet and the smooth surface of the particles reduces friction and prevents them gripping satisfactorily onto a surface on which they are crawling. For example, honey bee mites (Varroa) are prevented in this manner from crawling up the walls of the beehive and attaching to bees. They thus fall to the bottom of the hive and then are killed by an acaricide contained within the particles, by techniques known in the art.

In a preferred aspect of the present invention, a second pesticide or herbicide may be adhered to the coating of the electrically resistive material, i.e. on the outer surface of the composite particles.

Particles which have two pesticides associated therewith may have two possible modes of action on the same species of insect. For example, the pesticide impregnated into or associated with the inert substrate may be a bacillus which is toxic to the insect on ingestion. The second pesticide may be a fungus which is toxic by invasion through the outer cuticle of the insect.

The number of pesticides incorporated into a single particle may be regulated in order to achieve a desired range of target specificity, or particles having different constituents may be mixed to achieve the same end.

Alternatively, the composite particles of the present invention may contain a herbicide. For example, the herbicide may be a weedkiller which is sprayed onto a crop and will attach both to the crop plants and any weeds growing with the crop. The weedkiller then kills the weeds. Alternatively, the crop plants may be sprayed or dusted with herbicide containing particles to achieve another effect, such as promoting or delaying growth.

In situations where particular insect pests or fungal pests attack a crop, a suitable pesticide for the insect or fungi may be incorporated into the particles and the crop plants sprayed or dusted with the composition. The insects or fungal spores thus come into contact with the particles which adhere to them and the pesticide is released from the particles of the composition to kill the insects or fungal spores. Combined compositions comprising herbicides with insecticides and/or fungicides are contemplated within the scope of the invention.

Charging of the particles may be achieved by friction or by subjecting them to electrical discharge, high electrical fields or other suitable means. Where the particles are applied directly to the pest, plant or surface for instance, by a dispenser, such as, an aerosol spray dispenser, frictional charging may be effected by suitable design of the dispenser, particularly the nozzle configuration thereof.

The particles of the present invention will preferably retain their electrostatic charge for at least 24 hours when they contain slow acting chemical pesticides, such as chemical insecticides and for at least 4 to 5 days when they contain biological pesticides.

The present invention will be further described with reference to the accompanying drawings, in which:

FIG. 1 illustrates a particle of a control agent in accordance with the invention.

Referring to FIG. 1, the particle 4 comprises a highly absorbent or porous core 1 surrounded by an electrically resistive coating 2. The core 1 is impregnated with a pesticide, for example a biological insecticide such as *Metarhizium anisopliae*. The electrically resistive lipid coating may be, for example, carnauba Wax.

As illustrated in FIG. 1, the particle 4 has a further pesticide 3 applied to the outer surface of the coating 2. The further pesticide may comprise fungal spores. A plurality of particles as shown in FIG. 1 may be charged by corona discharge techniques.

The present invention will be further described with reference to the following Examples.

EXAMPLE 1

Silicon dioxide particles 0.5 to 10 $\mu$m in diameter, (Sigma Chemical Co.), 10 g, were mixed with log of the insecticide Sulfluramid (Trade Name—Griffin Corporation). Composite impregnated silicon dioxide particles were thus formed which were then throughly mixed with 80 g Carnauba wax particles of from 20 to 80 $\mu$m in diameter. The silica particles, which are known to occlude lipid materials acquired a coating of lipid molecules from the wax particles.

Carnauba wax is a highly electrically resistive material. Accordingly, the addition of the wax to the silica particles, and coating of the silica particles thereby, increases the level of charge imparted to the particles as a result of friction on shaking the powder.

10 adult German cockroaches (*Blattella germanica*) were treated with the prepared dry powder mixture using a fine camel hair brush to place a fine uniform coating over the whole of the dorsal surface of the insect. For each group of 10 insects that was treated with the mixture, a similar group was treated in exactly the same way with a mixture prepared in the proportions of silica, 90 g, and sulfluramid, 10 g. Each test was replicated four times with each group of 10 insects.

The treated cockroaches were kept in individual containers in a chamber at 25° C. and 30–40% relative humidity. The mortality of the insects was then recorded in terms of the number of insects out of 10 that showed no movement of any part of the body for 24 hours.

FIG. 2 shows the mean mortality of cockroaches from the four replicate tests. The results show that the insecticidal effect is significantly greater when the electrostatic properties of the carrier particles are increased by association with the wax particles. This is demonstrated by mortality occurring after 72 hours with the wax coated silica particles, rather than after than 96 hours for particles without the wax coating.

EXAMPLE 2

The procedure of Example 1 was repeated using chitosan (Seacure CL210, Pronova Biopolymer) as the carrier for the sulfluramid.

A control experiment was carried out substantially in the manner as described in Example 1 using a mixture of chitosan and sulfluramid.

The results of the experiments are given in FIG. 3, from which it can be seen that the insecticidal effect of the sulfluramid is increased when the carrier particles are coated with lipid.

EXAMPLE 3

The procedures of Examples 1 and 2 were repeated using adult American cockroaches (*Periplaneta americana*). Substantially the same results were obtained.

What is claimed is:

1. A pesticidal composition in particulate form which comprises composite particles having an average particle size in the range of from 1 to 100 μm, each particle comprising a core of an inert substrate having a first pesticide associated therewith, a coating of an electrically resistive material around said core, and a second pesticide adhered to the coating of electrically resistive material, the particles carrying an electrostatic charge.

2. A composition according to claim 1 wherein the particles have an average particle size in the range of from 20 to 60 μm.

3. A composition according to claim 1 wherein the inert substrate comprises silica, magnesium silicate, diatomaceous earth, cellulose or a natural or synthetic polymer.

4. A composition according to claim 1 wherein the first pesticide is an insecticide, fungicide, acaricide, insect growth regulator or chemosterilant.

5. A composition according to claim 1 wherein the first pesticide is a bacterium, virus or fungus.

6. A composition according to claim 1 wherein the first pesticide is a behaviour modifying chemical.

7. A composition according to claim 1 wherein the first pesticide comprises at least 0.1% by weight of the core of the particles.

8. A composition as claimed in claim 1 wherein the electrically resistance coating material comprises from 5 to 25% by volume of the particles.

9. A composition as claimed in claim 8 wherein the coating comprises a wax, a lipid, a natural or synthetic resin or a natural or synthetic polymer.

10. A composition as claimed in claim 1 wherein the second pesticide comprises fungal spores.

* * * * *